(12) United States Patent
Mantelmacher

(10) Patent No.: US 7,842,099 B2
(45) Date of Patent: Nov. 30, 2010

(54) PROSTHETIC ATTACHMENT SYSTEM WITH LOW PROFILE ATTACHMENT PAD

(76) Inventor: H. Lee Mantelmacher, 3704 Ashley Way, Owings Mills, MD (US) 21117

( * ) Notice: Subject to any disclaimer, the term of this patent is extended or adjusted under 35 U.S.C. 154(b) by 0 days.

(21) Appl. No.: 12/589,336

(22) Filed: Oct. 22, 2009

(65) Prior Publication Data

US 2010/0114331 A1 May 6, 2010

Related U.S. Application Data

(63) Continuation-in-part of application No. 11/496,707, filed on Jul. 31, 2006, now Pat. No. 7,771,487.

(60) Provisional application No. 61/196,988, filed on Oct. 22, 2008.

(51) Int. Cl.
*A61F 2/80* (2006.01)
(52) U.S. Cl. .................................... 623/34
(58) Field of Classification Search ............. 623/32–37
See application file for complete search history.

(56) References Cited

U.S. PATENT DOCUMENTS

| | | | | |
|---|---|---|---|---|
| 4,842,608 A | * | 6/1989 | Marx et al. | 623/33 |
| 5,653,766 A | * | 8/1997 | Naser | 623/33 |
| 6,793,682 B1 | * | 9/2004 | Mantelmacher | 623/36 |
| 7,727,284 B2 | * | 6/2010 | Warila | 623/36 |
| 7,771,487 B2 | * | 8/2010 | Mantelmacher | 623/34 |

* cited by examiner

*Primary Examiner*—Bruce E Snow
(74) *Attorney, Agent, or Firm*—Ober / Kaler; Royal W. Craig

(57) ABSTRACT

An anchoring system for a transtibial or transfemoral (above or below the knee) prosthesis. The anchoring system includes a liner for enveloping an amputee limb. The liner has a first strap releasably secured to the fabric of the liner by a reinforcement plate that has a particular molded hook backing that removably adheres to the liner in such a way as to still provide a secure anchor for the buckle. The liner also has a second strap fixedly attached to the distal bottom end of the liner. The anchoring system also includes a containment socket for seating the liner. The containment socket has a pair of slots there through at positions corresponding to the two straps of the liner, respectively. To apply the anchoring system, the patient first applies the liner to his/her limb. The liner is then inserted into the socket with the two fastening straps protruding out through the respective slots. The patient pulls down on the lower strap thereby drawing the liner down into the socket until the liner is securely seated in the socket. When fully seated, the two fastening straps are overlayed and secured to themselves by Velcro® or the lower strap is threaded through a buckle on the upper strap and secured onto itself with Velcro®. The foregoing forms a suspension which holds the prosthesis on. Moreover, the fastening straps through slots absolutely prevent lateral shift as well as rotation.

12 Claims, 4 Drawing Sheets

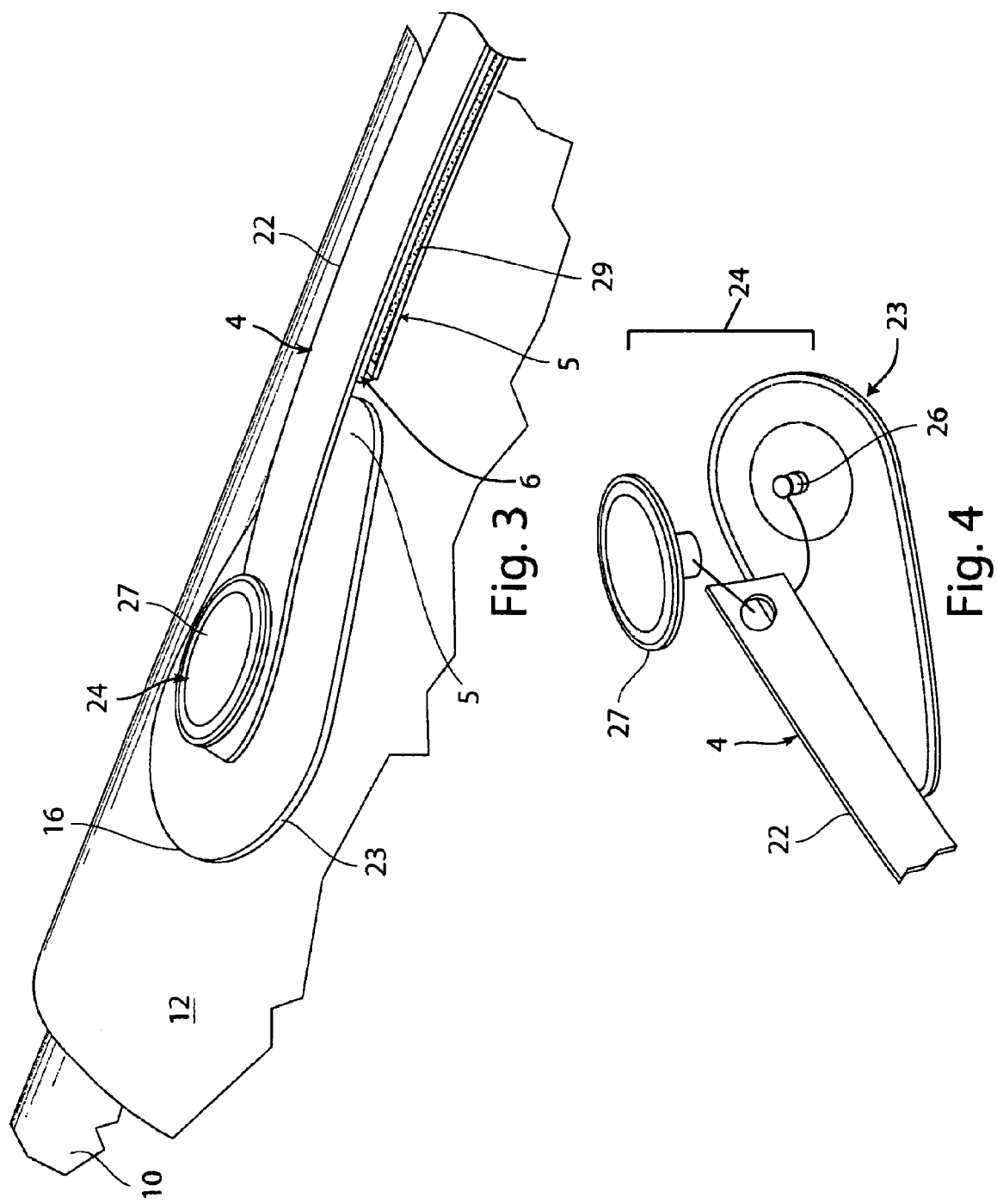

PROSTHETIC ATTACHMENT SYSTEM WITH LOW PROFILE ATTACHMENT PAD

CROSS-REFERENCE TO RELATED APPLICATION(S)

The present application derives priority from U.S. provisional application Ser. No. 61/196,988 filed Oct. 22, 2008, and is a continuation-in-part of U.S. application Ser. No. 11/496,707 filed Jul. 31, 2006 now U.S. Pat. No. 7,771,487.

BACKGROUND OF THE INVENTION

1. Field of the Invention

The present invention relates to prosthetics and, more particularly, to an anchoring system for post-operative prosthetic devices for above-the-knee amputation patients.

2. Description of the Background

There are a variety of different types of prosthetic devices for patients that have had either transfemoral (above-knee) or transtibial (below the knee) amputation. Typically, post-operative prosthetic devices for either type of amputation patients begin with a liner, which is rolled on to the residual limb. The liner is a soft, stretchy material that acts as an interface with the prosthesis.

Once the liner is on, the residual limb then slides into a hard socket. This socket is specially made to fit and can be made out of a variety of materials.

The hard socket for a transfemoral prosthesis has a knee joint connected to it, and the more fluid and natural the movement of the knee the better. Transtibial prosthetics have no knee joint. In both cases (with or without a knee joint) there typically is an aluminum or carbon fiber tube to which a foot module is connected.

For example, U.S. Pat. No. 5,653,766 to Naser issued Aug. 5, 1997 shows a prosthetic device 20 having a generally cylindrical socket 24 with an opening for receiving an amputated limb. The socket 24 is closed at the other end, and is mounted on a bendable knee joint. Once the limb is properly received within the socket 24, straps 38 are adjusted so that a secure fit is achieved. The patient then is able to walk using the prosthetic device 20.

With all such transfemoral and/or transtibial prosthetics (above & below the knee), it is very important that the socket be securely fitted to the limb and secured in place. Stability is a common problem as many existing anchoring systems use a single attachment point to hold the residual limb in place, and this typically leads to extraneous pivoting, rotation and shift during ambulation. Moreover, it is important to be able to adjust the anchoring system periodically because the mass of the limb may change significantly over the course of a day. The above-referenced '766 patent uses a radial pressure-fit imposed by tightening two belts. However, this tends to squeeze the limb unevenly and adds to discomfort. Moreover, the radial pressure tends to pop the limb out of the socket over the course of a day.

Another well-known ICEX® Socket System uses a combination lanyard and pin kit as a docking and locking mechanism. The socket has a distal pin that docks with the prosthesis. A lanyard is connected to the liner through a slot in the bottom of the socket. The lanyard is pulled to allow the patient's residual limb, which is enclosed in the silicone liner, to be drawn into the socket by the lanyard. The lanyard is then anchored to the front of the socket. The lanyard has the advantage of allowing for adjustment of position within the ICEX® Socket. If the limb changes position because of volume change and the distal migration of the limb into the socket, the prosthesis can easily be adjusted by the lanyard to compensate. The lanyard method of donning the socket also significantly reduces pain directly related to the donning process with a pin-locking mechanism. However, it has been found that many amputees lack the room for, are unable to tolerate, or have difficulty engaging the distal pin. Others complain of pain associated with engagement of the pin.

There are a number of "suspension" type sockets that eliminate the pin. U.S. Pat. No. 6,645,253 to Caspers issued Nov. 11, 2003 shows a suction system that employs a vacuum pump to impart suction to the liner, the vacuum pump doubling as a shock absorber for the artificial limb. Commercially, this is known as the Harmony® System which pulls air from the sealed socket and evacuates moisture (sweat) buildup. A nonporous polyurethane liner (not shown) is fitted over the residual limb and is inserted in the socket. A vacuum pump is attached via a connector block beneath the socket to create a vacuum force which is coupled by a tube to the liner, thereby evacuating air and sealing it to the residual limb. This provides a total-contact hypobaric suction equal weight distribution socket liner which tacks up to the skin of the residual limb and provides total contact with the limb.

U.S. Pat. No. 6,793,682 to Mantelmacher discloses a "Sure-fit Prosthetic Attachment System" (known commercially as the KISS® System) for a transfemoral and/or transtibial prosthesis, comprising a liner for enveloping an amputee limb. The liner has a strap attached at one end to a reinforcement plate that is sewn and/or bonded to the liner toward the top, and a buckle is attached to the other end of the strap and is suspended thereby from the liner. Another strap is fixedly attached to the bottom end of the liner. The anchoring system also includes a containment socket for seating the liner. The containment socket has a pair of slots there through at positions corresponding to the buckle and strap of the liner, respectively. To apply the anchoring system, the patient first applies the liner to his/her limb. The liner is then inserted into the socket with the fastening strap and buckle protruding out through the respective slots. The fastening strap is then threaded up through the buckle (running upward along the side of the socket) and are inserted there through. The patient pulls down on the strap and it works by pulley action to draw the liner down into the socket until the liner is securely seated in the socket. When fully seated, the fastening strap is secured to itself by Velcro®. The foregoing forms a suspension which holds the prosthesis on. Moreover, the fastening straps through slots absolutely prevent lateral shift as well as rotation. On the other hand, the patient need only readjust the Velcro® closure to adjust the position of the limb within the socket. Thus, if the limb changes position because of volume change and the distal migration of the limb into the socket, the prosthesis can easily be adjusted to compensate.

It has since been found that a design feature of the '682 patent can be significantly improved. Specifically, it would create a significant advantage from a manufacturing and ease-of-use standpoint to provide a like-functioning attachment system wherein the reinforcement plate securing the upper strap to the liner is removably adhered onto the liner in such a way as to still provide a secure anchor for the buckle.

SUMMARY OF THE INVENTION

Accordingly, it is an object of the present invention to provide an improved prosthetic anchoring system which increases the stability of the liner anchor using top-side and lower mechanical attachments to prevent all extraneous up and down motion, pivoting, rotation and shift.

It is another object to provide a prosthetic anchoring system with an unobtrusive low-profile substantially flush against the socket.

It is still another object to provide a prosthetic anchoring system as described above comprising a liner with a fabric exterior, a first strap releasably attached toward an upper end of the liner, and a second strap fixedly attached to the distal bottom end of the liner. The anchoring system also includes a containment socket for seating the liner, the containment socket including a pair of slots there through at positions corresponding to the two straps of the liner, respectively. The first strap is releasably secured to the fabric of the liner by a reinforcement plate that has a particular high-density molded hook backing that removably adheres to the liner in such a way as to still provide a secure anchor for the attached straps.

In accordance with the foregoing objects, the present device comprises an anchoring system for a transfemoral and/or transtibial prosthesis, comprising a liner for enveloping an amputee limb. The liner has a first strap releasably attached toward an upper end and secured to the fabric of the liner by a reinforcement plate that has a particular molded-hook backing that removably adheres to the liner in such a way as to still provide a secure anchor for the buckle. The liner also has a second strap fixedly attached to the distal bottom end of the liner. The anchoring system also includes a containment socket for seating the liner. The containment socket has a pair of slots there through at positions corresponding to the two straps of the liner, respectively. To apply the anchoring system, the patient first applies the liner to his/her limb, and then attaches the reinforcement plate onto the liner by pressing the hook backing against the liner fabric, thereby adhering it (removably) to the liner in such a way as to still provide a secure anchor for the first strap and suspended buckle. The liner is then inserted into the socket with the two fastening straps protruding out through the respective slots. The patient pulls down on the lower strap thereby drawing the liner down into the socket until the liner is securely seated in the socket. When fully seated, the two fastening straps are overlayed and secured to themselves by traditional hook-and-loop strips such as Velcro®.

The foregoing forms a suspension which holds the prosthesis on. Moreover, the fastening straps through slots absolutely prevent lateral shift as well as rotation. On the other hand, the patient need only readjust the Velcro® strap closure to adjust the position of the limb within the socket. Thus, if the limb changes position because of volume change and the distal migration of the limb into the socket, the prosthesis can easily be adjusted to compensate. The reinforcement plate may also be removed, repositioned and reattached on the liner as desired. It remains sandwiched between the liner and the socket when in use and this along with the particular molded hook backing helps to maintain it securely in place despite pulling on the strap, thereby providing a secure anchor for the buckle.

BRIEF DESCRIPTION OF THE DRAWINGS

Other objects, features, and advantages of the present invention will become more apparent from the following detailed description of the preferred embodiment and certain modifications thereof, in which:

FIG. 3 is a close-up view of the prosthetic anchoring system 2 as above showing the reinforcement plate 23 sandwiched between the liner 10 and the socket 12 as in normal use and maintaining the strap 4 securely in place.

FIG. 4 is a close-up view of grommet 24 sewn into the reinforcement plate 23.

DETAILED DESCRIPTION OF THE PREFERRED EMBODIMENTS

The present invention is a prosthetic attachment system for transfemoral and transtibial (above-knee and below-knee) amputees.

Figure 1:
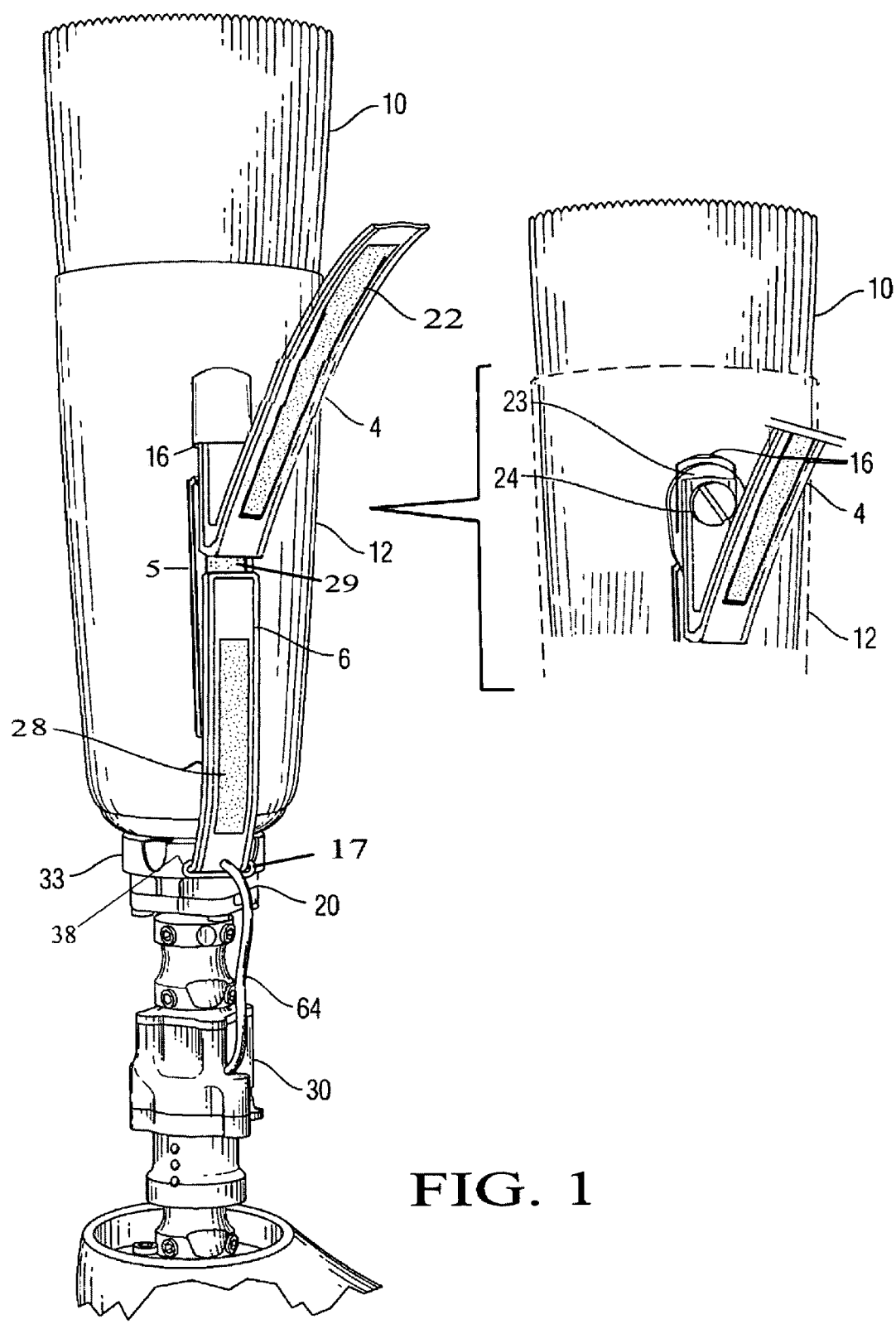
FIG. 1 is an illustration of the prosthetic anchoring system 2 according to one embodiment of the present invention with strap 4 unattached.

FIG. 1 is a perspective illustration of the prosthetic anchoring system 2 according to one embodiment of the present invention with first strap 4 unattached.

The anchoring system 2 generally includes a commercially-available liner 10 for enveloping the amputee's residual limb. Liner 10 is largely a standard transfemoral or transtibial suspension liner designed for amputees with amputations along the length of the tibia or femur. There are a variety of commercially-available suspension liners which will suffice, provided that they afford good suspension independent of volume fluctuations and provide a comfortable anatomical fit. These liners are typically formed of silicone or a gel blend with a fabric shell, and they may be equipped with a threaded socket assembly at the bottom for screw-insertion of a pin such as utilized in prior art pin securing assemblies. The fabric shell may be cotton, Nylon™, Lycra™ or other suitable woven fabric. The liner 10 and limb are then received in a conforming socket 12 that seats the limb. The socket 12 is a hard shell molded socket. For purposes of description, the drawing to the left of FIG. 1 shows the liner 10 obscured behind the socket 12, while the inset (right) details the liner 10 as it would appear behind the socket 12 (which is shown in dotted lines). In accordance with the present invention, the otherwise conventional liner is modified by retrofitting it with upper and lower straps 4, 6, respectively.

An upper strap 4 is secured to a reinforcement plate 23, and the reinforcement plate 23 is releasably secured on the outwardly facing side of the liner 10 (see inset). In the illustration, the reinforcement plate 23 includes an integral grommet 24, and upper strap 4 is pivotally attached at one end by grommet 24 to the reinforcement plate 23. The reinforcement plate 23 is a resilient member attached by a molded hook backing (as will be described) onto the fabric shell of liner 10 at an upper outside position as shown.

Figure 2:
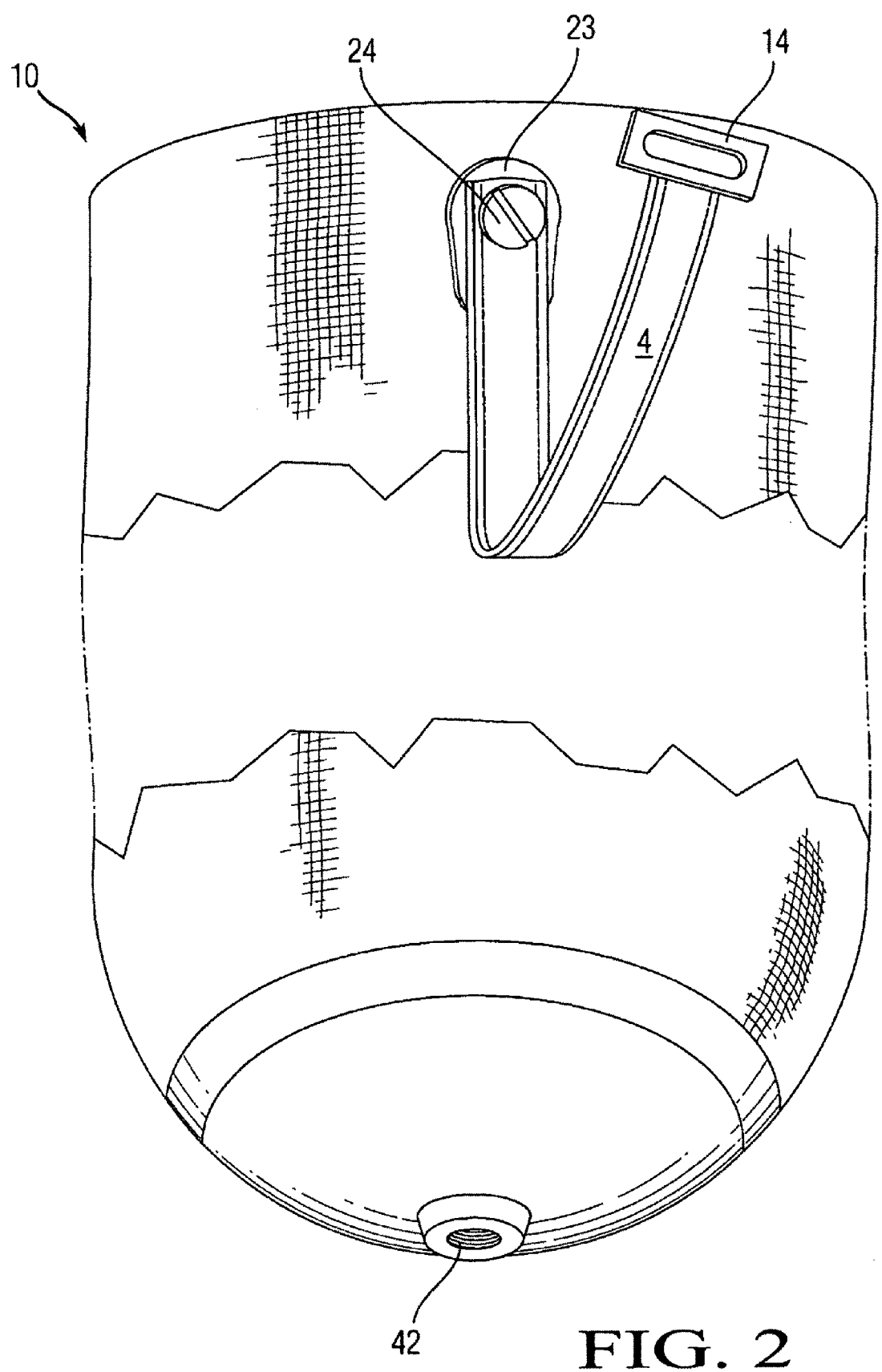
FIG. 2 is a view of the liner 10 with first strap 4 releasably attached toward an upper end and secured to the fabric of the liner by reinforcement plate 23 via hook-and-loop backing that removably adheres.

FIG. 2 is a view of the liner 10 with upper (first) strap 4 releasably attached as described. A lower (second) strap 6 is attached at one end to a threaded socket assembly at the bottom of the liner 10 such as by a pin or cap-screw threaded into receptacle 42.

Referring back to FIG. 1, the socket 12 is formed with at least one slot 16 passing through an upper side (at the outside of the limb) for allowing the upper strap 4 to pass outwardly there from. The socket 12 is also formed with one lower slot 17 (or aperture) at the bottom for allowing the lower strap 6 to pass outwardly there from. If the lower slot 17 is offset from center it should preferably be aligned with the upper slot 16. The liner 10 fits within the molded socket 12 and the socket 12 may include an integral (or separate) centering cup 33 having a pass-through slot 17 defined therein. The lower fastening strap 6 is threaded out through the lower slot 17 in the centering cup 33, and the upper fastening strap 4 is threaded out through the slot 16 in the socket 12. The lower fastening strap 6 is provided with a length of hook-and-loop (Velcro®) material 28 along its backside and extending out to the distal end. Similarly, the upper fastening strap 4 is provided with a length of hook-and-loop material 22 along its inside and extending down to the distal end. The socket 12 is also provided with a socket fastening strap 5 comprising a length of hook-and-loop material 29 running between the reinforcement plate 23 and centering cup 33.

Both upper and lower fastening straps 4, 6 as well as socket fastening strap 5 comprise approximately a 6-8" length of Nylon™ or Dacron™ braided strap, the lower strap 6 having opposing sections 28 of hook and loop material running to the respective tips on both sides, and the upper strap 4 having one section 22 of hook and loop material running to the respective tips on the inside. The socket fastening strap 5 is permanently adhered to the outside of socket 12 and comprises an outwardly-facing section 29 of hook and loop material running along its length. The lower fastening strap 6 is attached at one end to the bottom of liner 10. For example, existing liners may be equipped with a threaded socket assembly at the bottom end as shown and described in the '682 patent to Mantelmacher, which can be used to pivotally anchor the strap 4 thereto. When fully attached, the upper strap 4, lower strap 6 and socket fastening strap 5 form a three-layer Velcro® sandwich.

In general use, a patient will apply the liner 10 to their limb and then adhere the reinforcement plate 23 via molded hook backing to the upper outside position of the liner 10 as shown (the upper strap 4 already being attached to reinforcement plate 23 via grommet 24). The patient then inserts the liner 10 into the socket 12. The lower fastening strap 6 is threaded out through centering cup 33 and through lower slot 17, while upper strap 4 is passed out through upper slot 16.

FIG. 3 is a close-up view of the prosthetic anchoring system 2 as above showing the reinforcement plate 23 sandwiched between the liner 10 and the socket 12 as in normal use and maintaining the strap 4 securely in place. The lower fastening strap 6 is pulled out tight, and by its section of hook-and-loop material 28 it is releasably joined to the opposing hook-and-loop material 29 on the socket fastening strap 5. Then the upper fastening strap 4 is pulled down tight, and by its section of hook-and-loop material 22 it is releasably joined to the opposing hook-and-loop material 28 on the lower fastening strap 6. This forms a suspension which holds the prosthesis on and absolutely prevents lateral movement, pivotal shifting, and rotation. The particular components of the anchoring system 2 will now be described in more detail with reference to FIGS. 3-4.

FIG. 4 is a close-up view of reinforcement plate 23 for anchoring the grommet 24. The grommet 24 comprises two screw-together sections including a post 26 and cap 27 each having 1" flanges that sandwich the upper strap 4 there between. The flange of post 26 is sandwiched under a resilient plastic wafer, the plastic wafer being defined by a small hole for passing the neck of post 26. The neck of grommet 24 is inserted through the small hole, and both the plastic wafer and grommet 24 are sandwiched in this configuration and sewn between opposing vinyl sections (with stitching as shown around the outer margins as well as the grommet 24). Upper strap 4 is hole-punched at the distal end and is inserted over the protruding end of post 26, and the cap 27 is applied to secure the strap 4 on the post 26. The molded hook backing 25 of the reinforcement plate 23 is adhered to the vinyl section opposite the grommet 24.

Figure 5:
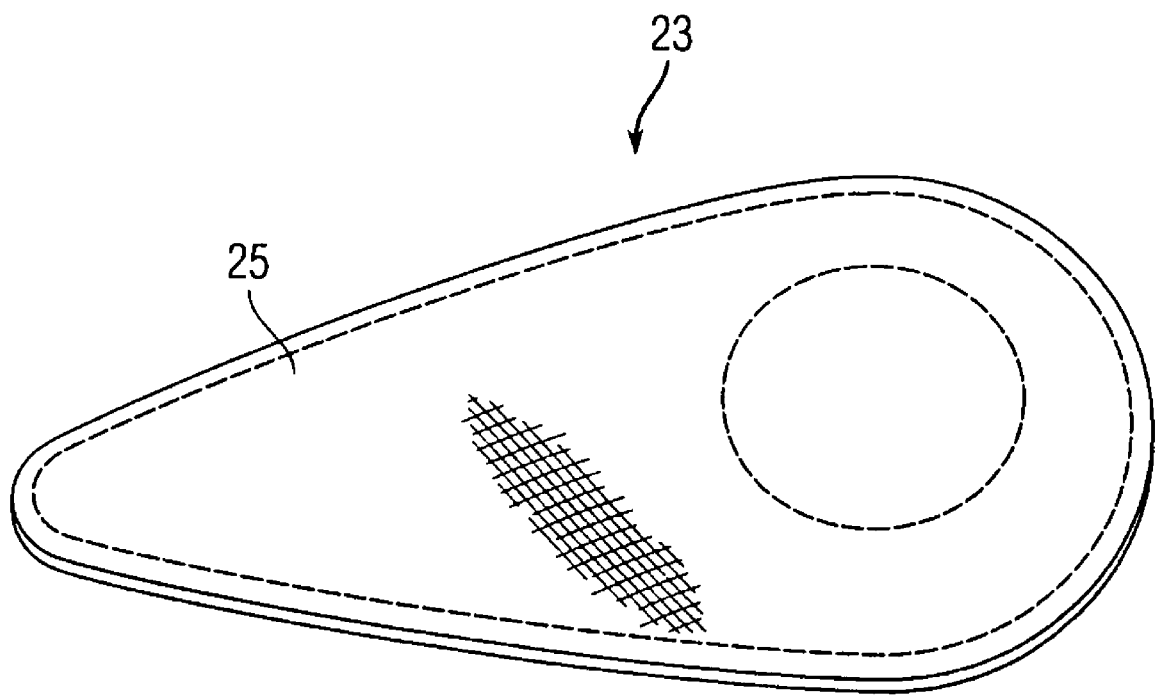
FIG. 5 is a close-up view of the molded hook backing 25 of the reinforcement plate 23.

FIG. 5 is a close-up view of the molded hook backing 25 of the reinforcement plate 23. The molded hook backing 25 is preferably a high-strength hook tape such as Velcro® ULTRA-MATE™ Brand High Technology Hook (HTH) webbing with a high 600-900 hook density per inch. More specifically, Velcro® Ultramate™ MVA8E has double headed hooks which have up to twice the gripping power of other hook specifications. The Velcro® Ultramate™ panel is RF-welded (or sewn) to the vinyl section of reinforcement plate 23. Ultramate™ has other advantages in that it is relatively low-profile and adheres to a wide variety of common woven fabrics. Thus, the reinforcement plate 23 may be releasably adhered to the fabric shell of the liner 10 without any bonding or sewing.

Typically, a patient will apply the anchoring system 2 by first applying the liner 10 to his/her residual limb. The patient then attaches the reinforcement plate 23 to the liner 10 (plate 23 already having upper strap 4 attached via grommet 24) by pressing the Velcro® Ultramate™ backing 25 into the fabric shell of the liner 10. The liner 10 is then partially inserted into the socket 12 until lower fastening strap 6 can be threaded through the slot 38 in centering cup 33 and on outward through the lower slot 17 through socket 12. In addition, the upper fastening strap 4 is passed outward through upper slot 16. The patient pulls down on the distal end of upper strap 4 which draws the liner 10 down into the socket 12 until the liner 10 is securely seated in the socket 12. When fully seated, the upper fastening strap 4 is overlayed atop the lower fastening strap 6, which is in turn overlayed atop the socket fastening strap 5, all being secured together by the opposing hook and loop sections 22, 28, 29.

One skilled in the art should understand that alternative strap configurations are possible without departing from the scope and spirit of the present invention. For example, the socket fastening strap 5 may be eliminated and the upper and lower fastening straps 4, 6 equipped with a higher-strength Velcro® for strips 22, 28, such as Velcro® Ultramate™. Alternatively, U.S. Pat. No. 6,793,682 to Mantelmacher discloses a "Sure-fit Prosthetic Attachment System" that attaches the two straps 4, 6 using a buckle rather than Velcro®, and this or any other attachment will suffice.

Having now fully set forth the preferred embodiments and certain modifications of the concept underlying the present invention, various other embodiments as well as certain variations and modifications of the embodiments herein shown and described will obviously occur to those skilled in the art upon becoming familiar with said underlying concept. It is to be understood, therefore, that the invention may be practiced otherwise than as specifically set forth in the appended claims.

I claim:
1. An anchoring system for a prosthesis, comprising:
a liner for enveloping an amputee limb, said liner being formed of elastomeric material with an outer fabric shell;
a pad having a hook-and-loop attachment surface on one side for attachment to said liner;
a first strap attached to said pad;
a second strap attached at a lower end of said liner; and
a socket for receiving said liner on said limb, said socket having a first upper slot there through for passing the first strap and a second lower aperture there through for passing the second strap.
2. The anchoring system for a prosthesis according to claim 1, wherein said first strap and said second strap include a fastening mechanism for attachment together.

3. The anchoring system for a prosthesis according to claim 2, wherein said first strap and said second strap both include a section of hook and loop material for attachment together.

4. The anchoring system for a prosthesis according to claim 3, further comprising a section of hook and loop material extending between said slots for binding the attached first and second straps to said socket.

5. The anchoring system for a prosthesis according to claim 1, wherein the pad's hook-and-loop attachment surface further comprises a high-density hook and loop surface.

6. The anchoring system for a prosthesis according to claim 1, wherein said pad includes a grommet protruding from another side opposite said hook-and-loop attachment surface, and said first strap is attached to the grommet.

7. The anchoring system for a prosthesis according to claim 1, further comprising a centering cup attached distally to said socket, said centering cup having a slot for passing the second strap.

8. An anchoring system for a prosthesis, comprising:
- a liner for enveloping an amputee limb, said liner being formed of silicon rubber with an outer woven fabric layer;
- an attachment pad comprising a reinforcing plate and grommet encased in a fabric pocket, and a hook-and-loop attachment surface attached on one side of said pocket for attachment to said liner;
- a first strap attached to said pad and extending to a first hook and loop section;
- a second strap attached at a lower end of said liner and extending to a second hook and loop section for attachment to the first hook and loop section of said first strap; and
- a hard shell socket conforming to said amputee limb for receiving said liner on said limb, said socket having an upper aperture for passing the first strap and a lower aperture for passing the second strap.

9. The anchoring system for a prosthesis according to claim 8, further comprising a third section of hook and loop material extending between said slots for binding the attached first and second straps to said socket.

10. The anchoring system for a prosthesis according to claim 8, wherein the pad's hook-and-loop attachment surface further comprises a high-density hook and loop surface.

11. The anchoring system for a prosthesis according to claim 8, wherein said grommet includes a mounting post protruding from another side opposite said hook-and-loop attachment surface, and said first strap is attached to the grommet.

12. The anchoring system for a prosthesis according to claim 8, further comprising a centering cup attached distally to said socket, said centering cup having a slot for passing the second strap.

* * * * *